United States Patent [19]

Feigenbaum

[11] Patent Number: 5,371,104

[45] Date of Patent: Dec. 6, 1994

[54] COMPOSITIONS CONTAINING FORSKOLIN

[76] Inventor: Jeffery J. Feigenbaum, 3600 N. Lake Shore Dr., Chicago, Ill. 60613

[21] Appl. No.: 198,536

[22] Filed: Feb. 18, 1994

Related U.S. Application Data

[63] Continuation of Ser. No. 826,287, Jan. 24, 1992, abandoned, which is a continuation of Ser. No. 489,961, Mar. 6, 1990, abandoned.

[30] Foreign Application Priority Data

Mar. 8, 1989 [IL] Israel .................................. 089.530

[51] Int. Cl.$^5$ ............................................. A61K 31/35
[52] U.S. Cl. .................................................... 514/455
[58] Field of Search ................................. 514/453, 455

[56] References Cited

U.S. PATENT DOCUMENTS

| | | | |
|---|---|---|---|
| 4,120,975 | 10/1978 | Orr et al. | 424/283 |
| 4,517,200 | 5/1985 | Kreutner et al. | 514/455 |
| 4,564,626 | 1/1986 | Kreutner et al. | 514/430 |
| 4,588,724 | 5/1986 | Greenway et al. | 514/250 |
| 4,724,238 | 2/1988 | Dohadwalla et al. | 514/455 |
| 4,782,082 | 11/1988 | Kreutner et al. | 514/454 |
| 4,871,764 | 10/1989 | Shutske | 514/455 |

OTHER PUBLICATIONS

Huang et al., "Inhibition of Forskolin-Activated Adenylate Cyclase by Ethanol and Other Solvents," *J. Cyclic Nucleotide Res.*, 8(6):385–394 (1982).
Chemical Abstracts: vol. 110 (25) 225312(t) (1989).
Chemical Abstracts: vol. 111(14) 120890(x) (1990).

*Primary Examiner*—Marianne M. Cintins
*Assistant Examiner*—T. J. Criares
*Attorney, Agent, or Firm*—Marshall, O'Toole, Gerstein, Murray & Borun

[57] ABSTRACT

The invention relates to a process for the solubilzation of forskolin, to the pharmaceutical compositions based on such solubilized forskolin and to the use of these in the treatment of various diseases and disorders and maladies in mammals, including human. Forskolin is 7-beta-acetoxy-8,13-epoxy-1-alpha,6-beta,9-alpha-trihydroxylabd-14-en-11-one.

3 Claims, No Drawings

COMPOSITIONS CONTAINING FORSKOLIN

This is a continuation of U.S. application Ser. No. 07/826,287, filed Jan. 24, 1992, now abandoned, which is a continuation of application Ser. No. 07/489,961 filed Mar. 6, 1990 now abandoned.

BACKGROUND OF THE INVENTION

The invention relates to solubilized forskolin (hereafter CHRL-1 being forskolin in solubilized form as described herein), and to its preparation. It further relates to pharmaceutical compositions containing such solubilized forskolin ingredient (i.e. CHRL-1).

Forskolin is a labdane diterpenoid, obtainable from natural sources by methanol extraction of the roots of *coleus forskoli*. The chemical name of forskolin is 7-beta-acetoxy-8,13-epoxy-1-alpha,6-beta,9-alpha-trihydroxylabd-14-en-11-one. The synthesis of forskolin is reported by S. D. Baltt, B. S., Bhawa, H. Dornauer, N. J. de Souza, and H. W. Fehlhaber, *Tetrahedron Letters* (1977); and by N. J. de Souza, A. N. Dohadwalla, and J. Reden *Med. Revs.*, vol. 3 (1983) pp. 201–219 and references cited therein. One commercial source of forskolin is Sigma Pharmaceutical Co., St. Louis, Mo. I believe that forskolin has not previously been used in vivo in the solubilized form described hereinafter.

SUMMARY OF THE INVENTION

I have found that forskolin is very soluble in dimethylacetate (DMA), and that this solution can be diluted with distilled water or saline for pharmaceutical use in the presence of a further additive, such as a non-ionic surfactant. A solution can also be made up with this solvent and an edible oil, for per os application; and also in non-edible oils. A further effective solvent is dimethyl-sulfoxide (DMSO), used together with a further additive such as a surfactant, as set out in detail hereinafter. A solution of forskolin can also be made up with DMSO and an edible oil for per os application, and also in non-edible oils for its administration by other routes.

The invention also relates to potent and long-lasting analgetic compositions which contain CHRL-1, and to pharmaceutical compositions containing CHRL-1 which are long acting and potent in counteracting the respiratory depression, hypothermia and addiction induced by morphine and by related narcotic compounds. Moreover, CHRL-1 has significant anti-depressant activity. CHRL-1 is also very active in inhibiting the psychotropic effects of high doses of delta$^1$-tetrahydrocannabinol (THC) and other cannabinoids contained within cannabis. Finally, the invention relates to compositions containing CHRL-1 which counteract the neuronal toxicity (and other toxicity), the behavioral aberrancies and the lethal effects induced by N-methyl-D-aspartate (NMDA) and resulting from NMDA receptor stimulation. Thus, my invention is useful in the treatment of various diseases and disorders and maladies in mammals, including humans.

DETAILED DESCRIPTION OF THE INVENTION

CHRL-1 can be prepared from the solvents listed above in the Summary or from other solvents. Amongst other possible solvents for forskolin there may be mentioned dipropylene glycol, ethylene glycol, formamide, dimethyl formamide, ethylene chloride, diethanolamine, triethanolamine, ethyl acetate, ethylmethoxyethanol, methyl chloride, methylene chloride, and dimethylamine. The limiting factor is one of physiological acceptability and possible toxicity. Considering these aspects, the first six members of this list are acceptable and can be used as solvents in the present invention. Such solvents can be used together with diacetylated monoglylcerides, dihydric alcohols including ethylene glycol, diethylene glycol, methylene glycol, propylene and dipropylene glycol; glyceryl mono-oleate, glyceryl monostearate, mono- or diglycerides; sucrose esters, as well as glycol, glycerol or polyoxyethelene esters; propylene glycol stearate, ethers (macrogol, macrogol lauryl, polyoxyl 20 cetostearyl and polyoxyoxyl 10 oleyl), octoxinols, poloxamers, polyvinyl alcohol, quillaia, saponin polysorbates, 20, 40, 60, 65, 80 and 85); and the sorbitans monolaurate, mono-oleate, monopalmitate, monostearate, sesquiolate trioleate, tristearate; and sorbitan derivatives, all of which may be used by themselves or together with DMA or DMSO.

The preferred systems are those of DMSO with a suitable surfactant or DMA with such surfactant.

When DMSO is used, the solubilization is effected by contacting a certain quantity of forskolin and the solvent, vortexing at high speed so as to dissolve the forskolin and adding a suitable active agent such as Emulphor (polyoxyethylated vegetable oil); vortexing again until a clear solution is obtained, and diluting same with a desired quantity of water or saline.

For example, 50 mg forskolin is mixed with 0.4 mn DMSO, vortexed at high speed for 2 minutes; 0.4 ml Emulphor or another non-ionic surfactant is added followed by further vortexing until a clear solution is obtained, with 1.7 ml water or saline added to result in a clear solution containing about 20 mg/ml containing about 16% DMSO and about 16% Emulphor.

As a further example, 2.5–4.5 mg. forskolin is added to 0.5 mn of DMA in a small (4 ml) vial, completely covering all of the drug with the solvent. When the drug is completely dissolved, 0.10 ml of a non-ionic surfactant is added (preferably Tween 20, a polyoxyethylene sorbitan monooleate or Emulphor El-620, a polyoxyethylated vegetable oil). Heating is unnecessary. The forskolin, dissolved in DMA, is thoroughly integrated into the surfactant by turning the vial on its side and rotating slowly, allowing the DMA-containing forskolin and the surfactant to mix together while coating the sides of the vial. The rotation should take 3–3.5 min. Following this, dilution is effected as required with distilled water or saline followed by vortexing at maximum speed for 2–3 min.(The same technique for integrating the forskolin into the surfactant may also be employed when using DMSO as a solvent).

The solubilized form of forskolin (i.e. CHRL-1) results in a stimulation of adenylate cyclase activity at dosages 10 to more than 20 times lower than that of the drug in suspension, without any apparent side effects in animals administered 1 $\mu$g/kg to 1 mg/kg of CHRL-1 in vivo. When, in contrast, forskolin is administered in vivo om the form of a suspension, the dosage required to stimulate adenylate cyclase is about 20 mg/kg, with behavioral disturbances resulting, including either sedation, or head twitches and motor stereotypies (q.v. Wachtel et al., Neurosci. Lett. 76: 191–196 (1987).

CHRL-1 in doses in 1 $\mu$g/kg provides very potent analgesia in both inbred (C-57/B-1) and outbred (Sabra) mice, as well as in rats (Sabra; an outbred strain). The analgesia is equivalent to 10–20 mg/kg of morphine but unlike the latter, is not accompanied by sedation, or marked hypothermia and respiratory depression. Moreover, unlike morphine induced analgesia, the antinociceptive activity of CHRL-1 lasts over 24 hours, and is characterized by very low tolerance and addiction potential. These effects are summarized in Tables 1 and 2 below.

The same doses of CHRL-1 also completely reverse the respiratory depression induced by a high (25 mg/kg) dose of morphine within 15–20 min. of the administration of CHRL-1; with respiration increasing from about 65% of normal, to slightly over 100% of normal. Moreover, pretreatment with a 50 μg/kg dose of CHRL-1 48 h. prior to the same dose of morphine (25 mg/kg) was seen to completely protect rats so injected from undergoing any significant change in respiration (see Tables 1.1.1. and 1.1.2. below). The same doses of CHRL-1 (1μg/kg to 150 μg/kg) also significantly reversed the hypothermia induced by morphine (25.0 mg/kg) within 15 minutes, from about $-2°$ C. to $-0.8°$ C. (the highest dose of 150 μg/kg being less effective than 1 and 50 μg/kg). The hypothermia was completely reversed by all doses of CHRL-1 administered within 1 hr. of its administration at a time when control animals receiving only morphine had a core body temperature 2.2° C. below normal (see Table 2 below).

The same doses of CHRL-1 (1 μg/kg to 500 μg/kg) also markedly inhibited the 'dispair' of rats in a forced swimming paradigm of anti-depressant activity by as much as 50% relative to control (See Table 3 below). The same doses of CHRL-1 (1 and 50 μg/kg) also significantly inhibited the tremor, seizure and death induced by N-methyl-D-Aspartate (115 mg/kg) with the lower dose of CHRL-1 being totally effective (see Table 4 below). The same doses of CHRL-1 (1 μg/kg) induced a nearly complete supression of naloxone-precipitated jumping in mice addicted to morphine by pellet implantation (75 mg. morphine over 72 h.), in a small group of animals.

A 50 μg/kg dose of CHRL-1 also completely reversed the psychotropic effects induced by an extremely high (25 mg/kg) dose of $\Delta^1$-tetrahydrocannabinol in both inbred (C-57/B-1) and outbred (Sabra) mice, as measured by the Ring Test of Pertwee. CHRL-1 reduced the $\Delta^1$-THC elicited elevations of the psychotropic index by up to 58–59%, to control levels (see Table 4). CHRL-1 solution stored at ambient temperature for 6 months was used for repeat tests and compared with fresh solutions. No reduction in activity was observed. It should be noted that all of the activities of CHRL-1 discussed above and summarized in the tables below were observed following the administration of a solution prepared with DMSO and emulphor. This solution is clear and essentially odorless, and has a pH of . when made up to a concentration of 50 μg/ml. The solution freezes at 0° C. and has a boiling point of about 94° C. At. 42° C. it is stable and can be stored at room temperature for at least one month without refrigeration.

As it may be seen from Tables A and B below, the doses of CHRL-1 at which optimal activity is seen (i.e. 1 and 50 μg/kg) contain about 0.0009% and 0.047% DMSO respectively, and 0.002 and 0.06DMA respectively. DMSO is currently being used as a vehicle for drugs such as idoxuridine and is available for human use as a 50% solution in the USA (as Rimso-50; ® Research Industries Corp.) and as a 70% solution in Canada (as Kemsol ®, Horner). The safety of DMSO as a solvent or as a drug in its own right for human use is discussed by Mason (in Dimethyl Sulfoxide, Vol. 1, Marcel Dekker, Inc., New York, 1971) and by Swanson (Rev. Clin. Basic Pharmacol. 5: 1–33 (1985). DMA is currently used as a solvent in drugs and other pharmaceutical products (Martindale's, 28$^{th}$ Ed., 1982) and is less toxic than dimethylformamide (Ibid.), which Bristol Myers has included in one of its patents for cis-platinum.

TABLES

The Tables A and B below give the volume and % of water, solvent and surfactant for various solutions of CHRL-1. In each solution, the absolute amount of solvent (DMSO or DMA) and surfactant remains constant.

TABLE A

| Amt. of CHRL-1 added to solution | Total vol. of solution | Vol. of water in solution | Vol. of DMSO + surfactant | | Drug conc. (mg/kg) | In Solution | |
|---|---|---|---|---|---|---|---|
| | | | | | | % of DMSO | % of surfactant |
| 50 mg. in | 2.5 ml | (1.7 ml | + 0.80 ml) | = | 20.0 | 16.0 | 16.0 |
| | 5.0 | 4.2 | 0.80 | | 10.0 | 8.0 | 8.0 |
| | 10.0 | 9.2 | 0.8 | | 5.0 | 4.0 | 4.0 |
| | 20.0 | 19.2 | 0.8 | | 2.5 | 2.0 | 2.0 |
| | 40.0 | 39.2 | 0.8 | | 1.25 | 1.0 | 1.0 |
| | 80.0 | 79.2 | 0.8 | | 0.625 | 0.5 | 0.5 |
| | 160.0 | 159.2 | 0.8 | | 0.312 | 0.25 | 0.25 |
| | 320.0 | 319.2 | 0.8 | | 0.156 | 0.125 | 0.125 |
| | 640.0 | 639.2 | 0.8 | | 0.078 | 0.0625 | 0.0625 |
| | liters | liters | | | | | |
| | 1.28 | 1.2792 | 0.8 | | 0.039 | 0.0312 | 0.0312 |
| | 2.56 | 2.5592 | 0.8 | | 0.0195 | 0.0156 | 0.0156 |
| | 5.12 | 5.1192 | 0.8 | | 0.0097 | 0.0078 | 0.0078 |
| | 10.24 | 10.2392 | 0.8 | | 0.0048 | 0.0039 | 0.0039 |
| | 20.48 | 20.4792 | 0.8 | | 0.0024 | 0.0019 | 0.0019 |
| | 40.96 | 20.9592 | 0.8 | | 0.0012 | 0.0009 | 0.0009 |

TABLE 8

In each solution below, the absolute amount of DMA and surfactant (present in a 1:2 ratio) remains constant, i.e. 0.05 ml DMA and 0.10 ml detergent.

| Amt of CHRL-1 added to solution | Total vol. of solution (ml) | Vol. of water in solution (ml) | | Vol. of DMA + surfactant (ml) | | Drug conc. (mg/kg) | In Solution: % of DMA | % of sur- factant |
|---|---|---|---|---|---|---|---|---|
| 3.75 mg in | 0.15 | (0.00 | + | 0.15) | = | 25.0 | 33 | 66 |
| | 0.30 | (0.15 | + | 0.15) | = | 12.5 | 16 | 32 |
| | 0.60 | (0.45 | + | 0.15) | = | 6.25 | 8 | 16 |
| | 1.20 | (1.05 | + | 0.15) | = | 3.12 | 4 | 8 |
| | 2.40 | (2.25 | + | 0.15) | = | 1.56 | 2 | 4 |
| | 4.80 | (4.65 | + | 0.15) | = | 0.78 | 1 | 2 |
| | 9.60 | (9.45 | + | 0.15) | = | 0.39 | 0.5 | 1 |
| | 19.20 | (19.05 | + | 0.15) | = | 0.195 | 0.25 | 0.5 |
| | 38.40 | (38.25 | + | 0.15) | = | 0.0975 | 0.125 | 0.25 |
| | 76.80 | (76.65 | + | 0.15) | = | 0.0487 | 0.0625 | 0.125 |
| | 153.60 | (153.45 | + | 0.15) | = | 0.0243 | 0.0317 | 0.0625 |
| | 307.20 | (307.05 | + | 0.15) | = | 0.0121 | 0.0158 | 0.0317 |
| | 614.40 | (614.25 | + | 0.15) | = | 0.0060 | 0.0079 | 0.0158 |
| | 1228.80 | (1228.65 | + | 0.15) | = | 0.0030 | 0.0039 | 0.0079 |
| | 2457.60 | (2457.45 | + | 0.15) | = | 0.0015 | 0.0019 | 0.0039 |

The TABLES 1 to 6 DIVERSE ACTIVITY OF CHRL-1 IN VIVO

TABLE 1

ANALGESIA: ACUTE EFFECT

Analgesia was assayed by means of the two most widely used tests of antinociception extant; viz. the tail flick and hot plate tests of analgesia.

1.1. Tail Flick

A photocell beam interrupted by a flick of the tail automatically stopped a digital timer to within a tenth of a second of the time of the first tail flick. The intensity of the nociceptive stimulus was adjusted to a mean latency of $5 \pm 0.5$ sec. in control (vehicle injected) animals. Each animal was tested only once to either the first tail flick or to a cut-off of 15 sec. (greater latencies being unduly traumatic to the tail). Data from animals with ambiguous tail movements (i.e. not a crisp, well-defined flick) were discarded. Data presented as mean latency in secs. $\pm$ S.E.M.

1.1.1. Statistical Analysis

| DOSE OF DRUG (mg/kg) | SPECIES TESTED | STRAIN TESTED | N | FORSKOLIN LATENCY $\overline{X}$ | $\pm$ | SEM | MORPHINE LATENCY $\overline{X}$ | $\pm$ | SEM | N | DOSE OF MORPHINE (mg/kg) | MORPHINE LATENCY $\overline{X}$ | $\pm$ | SEM | SEDATION PRESENT |
|---|---|---|---|---|---|---|---|---|---|---|---|---|---|---|---|
| 0.00 | MOUSE | C-57/B | 7 | 4.3 | | 0.3 | 5.2 | | 0.3 | 7 | 2.50 | 12.2 | | 1.2 | + |
| | | SABRA | 7 | 4.8 | | 0.6 | 4.8 | | 0.6 | 7 | | — | | — | + |
| | RAT | SABRA | 7 | 5.1 | | 0.5 | 5.1 | | 0.5 | 6 | | 12.7 | | 1.1 | + |
| 0.001 | MOUSE | C-57/B | 5 | 14.2 | | 0.6 | 5.3 | | 0.7 | 5 | 6.25 | 14.0 | | 1.0 | ++ |
| | | SABRA | 5 | 14.4 | | 0.5 | — | | | | | — | | — | |
| | RAT | SABRA | 5 | 14.9 | | 0.1 | 5.2 | | 0.6 | 5 | | | | | |
| 0.05 | MOUSE | C-57/B | 10 | 14.9 | | 0.1 | 7.2 | | 1.1 | 5 | 10.00 | 14.9 | | 0.1 | +++ |
| | | SABRA | 8 | 14.5 | | 0.5 | — | | | | | | | | |
| | RAT | SABRA | 6 | 14.2 | | 0.4 | 7.0 | | 1.0 | 5 | | 14.6 | | 0.3 | +++ |
| 0.20 | RAT | SABRA | 5 | 13.2 | | 0.7 | 10.2 | | 1.1 | 5 | | | | | |
| 1.00 | MOUSE | C-57/B | 5 | 13.6 | | 0.6 | 10.8 | | 1.0 | 5 | | | | | |
| | | SABRA | 5 | 13.8 | | 0.7 | 11.0 | | 0.9 | 5 | | | | | |

NOTE:
Doses of morphine >10.0 mg/kg induced no greater analgesia but only increased the intensity of sedation. No dose of CHRL-1 induced any sedation

| DOSE OF FORSKOLIN (MG/KG) | SPECIES TESTED | STRAIN TESTED | N | FORSKOLIN LATENCY $\overline{X}$ | $\pm$ | SEM | MORPHINE LATENCY $\overline{X}$ | $\pm$ | SEM | N |
|---|---|---|---|---|---|---|---|---|---|---|
| 0.00 | MOUSE | C-57/B | 6 | 9 | | 1 | 9 | | 1 | 6 |
| | | SABRA | 6 | 12 | | 1 | | | | |
| | RAT | SABRA | 6 | 12 | | 1 | 11 | | 1 | 6 |
| 0.001 | MOUSE | C-57/B | 5 | 19 | | 3 | 10 | | 1 | 5 |
| | | SABRA | 5 | 35 | | 4 | | | | |
| | RAT | SABRA | 5 | 27 | | 1 | 12 | | 1 | 5 |
| 0.05 | MOUSE | C-57/B | 5 | 24 | | 2 | 12 | | 1 | 5 |
| | | SABRA | 5 | 38 | | 2 | | | | |
| | RAT | SABRA | 5 | 28 | | 1 | 11 | | 1 | 5 |
| 0.20 | RAT | SABRA | 5 | 26 | | 2 | 16 | | 2 | 5 |
| 1.00 | MOUSE | SABRA | 5 | 28 | | 2 | 22 | | 2 | 5 |

TABLE 2

ANALGESIA: CHRONIC EFFECT (OVER 24 HOURS)

In addition to measuring the acute effects of forskolin on analgesia (within 1 h. of its administration), the solublized form of forskolin described herein was also used in chronic tests of analgesia, wherein C-57/B and Sabra mice were administered forskolin and tested only once either 1 h. or 24 h. subsequently.

| HOURS POST ADMINISTRATION | DOSE OF FORSKOLIN | SPECIES | STRAIN | N | FORSKOLIN LATENCY $\bar{X}'$ | ± | SEM | MORPHINE LATENCY $\bar{X}$ | ± | SEM | N |
|---|---|---|---|---|---|---|---|---|---|---|---|
| 2.1. Tail Flick | | | | | | | | | | | |
| 2.1.1. Statistical Analysis | | | | | | | | | | | |
| 1.0 | 0.00 | MOUSE | C-57/B | 7 | 5.2 | | 0.3 | 5.2 | | 0.3 | 7 |
| 1.0 | 0.05 | MOUSE | C-57/B | 5 | 14.4 | | 0.4 | 5.0 | | 0.5 | 5 |
| 24.0 | 0.05 | MOUSE | C-57/B | 5 | 14.5 | | 0.5 | 5.1 | | 0.4 | 5 |
| 24.0 | 10.00 | MOUSE | C-57/B | | — | | | 6.4 | | 0.9 | 5 |
| 2.2. Hot Plate | | | | | | | | | | | |
| 2.2.1. Statistical Analysis | | | | | | | | | | | |
| 1.0 | 0.00 | MOUSE | SABRA | 6 | 12 | | 1 | 12 | | 1 | 6 |
| 1.0 | 0.05 | MOUSE | SABRA | 5 | 38 | | 2 | 12 | | 1 | 5 |
| 24.0 | 0.05 | MOUSE | SABRA | 5 | 33 | | 5 | 11 | | 1 | 5 |
| 24.0 | 10.00 | MOUSE | SABRA | | — | | | 13 | | 1 | 5 |

TABLE 3

INHIBITION OF NARCOTIC INDUCED RESPIRATORY DEPRESSION, HYPOTHERMIA AND WITHDRAWAL SYMPTOMS/ADDICTION BY FORSKOLIN

CHRL-1, the solublized form of forskolin described herein, provides a prompt, prolonged and potent inhibitory action against the major side effects of narcotics such as morphine while not interfering with or actually potentiating their analgesic activity.

1. RESPIRATORY DEPRESSION
    1.1. Respiratory Frequency
        1.1.1. Short-Term Experiments Sabra rats were randomly assigned to one of 4 sub-groups, receiving morphine alone (25.0 mg/kg), or morphine followed 30 min. subsequently by one of 3 doses of CHRL-1 (viz. 0.001, 0.05, or 0.15 mg/kg, s.c.). All animals were observed for 90 min. The basal respiratory rate of each animal ($R_f$) was determined 60 min. following their habituation in a metal cage at a time when the animals were seen to lie quietly in their cages. $R_f$ was measured as distinct, individual displacements of the thorax in a 15 sec. interval as determined by visual observation, with each interval measured by a stopwatch accurate to 0.1 sec. The respirations observed per 15 sec. interval were multiplied by a factor of 4 to give an $R_f$ in respirations per minute.

| DOSE OF FORSKOLIN (MG/KG) | TIME POST MORPHINE PRETREATMENT | | | | |
|---|---|---|---|---|---|
| | 0 MIN. | 30 MIN. | 45 MIN. | 90 MIN. | |
| | TIME POST FORSKOLIN ADMINISTRATION | | | | |
| | 0 MIN. | 0 MIN. | 15 MIN. | 60 MIN. | (N) |
| 0 | 125 ± 4 | 91 ± 13 | 87 ± 12 | 80 ± 8 | 6 |
| 0.001 | 128 ± 9 | 90 ± 8 | 122 ± 6 | 133 ± 6 | 6 |
| 0.05 | 126 ± 5 | 93 ± 6 | 124 ± 5 | 129 ± 4 | 6 |
| 0.15 | 129 ± 5 | 96 ± 4 | 127 ± 5 | 135 ± 8 | 6 |

1.1.2. Long-Term Experiments

Sabra rats were pretreated with saline (0.9%, s.c.), and subsequently administered CHRL-1 (0.05 mg/kg, s.c.; 1 h. later). 48 h. following the injection of CHRL-1, the animals were administered morphine (25.0 mg/kg) at the same time that the animals in the acute study described above (q.v. 1.1.1) received morphine. Consequently, the control group from the acute study served as the control group of the chronic study. Both control and forskolin injected groups were then examined for 90 min.

| DOSE OF FORSKOLIN (MG/KG) | TIME POST FORSKOLIN PRETREATMENT | | | | |
|---|---|---|---|---|---|
| | 0 MIN | | 2880 MIN. | | |
| | TIME POST MORPHINE ADMINISTRATION | | | | |
| | 0 MIN. | 30 MIN. | 60 MIN | 90 MIN. | (N) |
| 0 | 125 ± 4 | 91 ± 13 | 87 ± 12 | 80 ± 8 | 6 |
| 0.05 | 128 ± 7 | 110 ± 11 | 121 ± 4 | 116 ± 7 | 6 |

1.2. Blood Gas Analysis

Basal $R_f$ measurements were taken for Sabra rats subsequently pretreated with morphine (25.0 mg/kg, s.c.), followed 1 h. later by CHRL-1 (0.05 mg/kg, s.c.). Subsequently, all animals were administered 0.3 ml per 100 g. of an anesthetic solution. Polyethylene catheters were introduced into the carotid artery for blood samples. Subsequent experiments (now in progress) will also include cannulation of the external jugular vein for measurements of pulse and blood pressure using a polygraph and calibrated pressure transducers. Each blood sample was analyzed by an automatic continuously recalibrated blood gas analyzer, for pH, $pCO_2$, $pO_2$, $HCO_3^-$, and B.E. (base excess). Typical values are presented.

| MIN. TIME POST FORSKOLIN INJECTION | TIME POST MORPHINE INJECTION | $R_f$ (per min.) | pH | $pCO_2$ (mm Hg) | $pO_2$ (mm Hg) | $HCO_3^-$ (mmol/l) | B.E. (mmol/l) |
|---|---|---|---|---|---|---|---|
| 0 | 0 | 134 | 7.22 | 20.3 | 133.5 | 8.5 | −16.7 |
| 0 | 30 | 102 | 7.32 | 26.0 | 127.1 | 13.6 | −9.8 |

TABLE 3-continued

INHIBITION OF NARCOTIC INDUCED RESPIRATORY DEPRESSION,
HYPOTHERMIA AND WITHDRAWAL SYMPTOMS/ADDICTION BY FORSKOLIN

| 0 | 60 | 91 | 7.29 | 32.8 | 127.4 | 15.8 | −8.9 |
|---|---|---|---|---|---|---|---|
| 20 | 70 | 136 | 7.24 | 28.1 | 129.3 | 11.3 | −14.5 |
| 30 | 90 | 139 | 7.20 | 18.2 | 128.5 | 6.5 | −21.3 |
| 120 | 180 | 136 | 7.21 | 20.8 | 128.1 | 8.0 | −18.2 |

2. HYPOTHERMIA

Sabra rats were randomly divided into one of 4 groups. The core (rectal) temperature of each animal was determined, whereupon each was pretreated with 25 mg/kg morphine HCl (s.c.). 30 min. following morphine, animals were administered CHRL-1 in doses of 0.00 (controls), 0.001, 0.05 or 0.15 mg/kg), and their core temperatures measured over a 90 min. period from the time of their first injection. Results below are given as the mean temperature (in °C.) per time period ± SEM.

| | | TIME POST MORPHINE ADMINISTRATION | | | | | | |
|---|---|---|---|---|---|---|---|---|
| | | 0 MIN. | | 30 MIN. | | 45 MIN. | | 90 MIN. |
| DOSE OF | | TIME POST FORSKOLIN ADMINISTRATION | | | | | | |
| FORSKOLIN | N | 0 MIN. | | 0 MIN. | | 15 MIN. | | 60 MIN. |
| 0. | 6 | 37.6 | .3 | 35.5 | .6 | 35.7 | .8 | 35.4 .5 |
| 0.001 | 6 | 37.5 | .2 | 35.2 | .4 | 36.7 | .3 | 37.0 .3 |
| 0.05 | 6 | 37.7 | .3 | 35.6 | .3 | 36.9 | .1 | 37.5 .2 |
| 0.15 | 6 | 37.5 | .1 | 35.7 | .5 | 36.4 | .2 | 37.3 .1 |

3. ADDICTION

In a pilot study, Sabra mice were implanted subcutaneously with pellets of morphine HCl, each containing 75 mg. A constant slow release of the morphine was effected by the body heat of the animal over a 72 h. period. The presence of addiction was subsequently determined by the appearance of the withdrawal symptoms of precipitated abstinance (jumping and vocalizing) induced by naloxone (0.8 mg/kg). Preliminary results with CHRL-1 (0.05-1 mg/kg) indicate a very marked-to nearly complete supression of morphine withdrawal. Data are not presented due to the small number of animals per group (n = 3), and these results are to be regarded as tentative albeit extremely encouraging. A full-scale, protracted study using doses of CHRL-1 ranging from 0.001 to 1.0 mg/kg before, during and/or after pellet implantation will be implemented shortly.

TABLE 4

INHIBITION OF THE CANNABIMIMETIC (PSYCHOTROPIC) EFFECT OF $\Delta^9$-TETRAHYDROCANNABINOL (THC)

The Mouse Ring Test of Pertwee (1972) was used to assess the effect of CHRL-1 on the psychotropic activity of an extremely high dose of THC (25.0 mg/kg). One hour following the administration of either vehicle, CHRL-1 (0.05 mg/kg), THC (25.0 mg/kg) or CHRL-1 (0.05 mg/kg) + THC (25 mg/kg) Animals were randomly assigned to one of 4 treatment groups receiving either vehicle alone, CHRL-1 (0.05 mg/kg), THC (25 mg/kg), CHRL-1 (0.05 mg/kg) + THC (25 mg/kg) administered simultaneously, or CHRL-1 (0.05 mg/kg) followed 1 h. later by THC (25 mg/kg). 90 min. following the injection of either vehicle, CHRL-1 alone or THC (in the last two groups with CHRL-1, or by itself). C-57 mice were placed upon the rim of a laboratory ring stand 6 cm in diameter situated 25 cm above a horizontal surface.

The movement of each mouse on the metal ring was then constantly monitored for each episode of complete dormancy (excluding slight head movements due to breathing) over a 5 min. period. The total time of dormancy on the ring was calculated as an index expressed as the % of total time of complete dormancy observed ($T_D$) where $T_D$ = duration of dormancy (in sec.)/ 300 sec. × 100. When Sabra mice were used, the same procedure as above was followed with the sole exception of THC being administered 1 h. prior to CHRL-1 (and hence the animals were tested 90 min. following CHRL-1).

| STRAIN | DRUG | DOSE (MG/KG) | INDEX (%) | N | |
|---|---|---|---|---|---|
| C-57/B | Vehicle | — | 11 ± 1 | 10 | |
| | CHRL-1 | 0.05 | 11 ± 2 | 17 | |
| | $\Delta^1$-THC | 25.00 | 72 ± 5 | 10 | |
| | CHRL-1 | 0.05 | 13 ± 1 | 10 | ← CHRL-1 pretreatment 1 h. pre-THC |
| | + | | | | |
| | $\Delta^1$-THC | 25.00 | | | |
| | CHRL-1 | 0.05 | 16 ± 3 | 8 | ← CHRL-1 injected simultaneously with THC |
| | + | | | | |
| | $\Delta^1$-THC | 25.00 | | | |

TABLE 4-continued

INHIBITION OF THE CANNABIMIMETIC (PSYCHOTROPIC) EFFECT OF $\Delta^9$-TETRAHYDROCANNABINOL (THC)

| SABRA | Vehicle | — | 12 ± 1 | 10 |
|---|---|---|---|---|
| | CHRL-1 | 0.05 | 14 ± 2 | 6 |
| | $\Delta^1$-THC | 25.00 | 73 ± 6 | 6 |
| | $\Delta^1$-THC | 25.00 | 15 ± 3 | 7 |
| | + | | | |
| | CHRL-1 | 00.05 | | |

TABLE 5

ANTI-DEPRESSANT PROPERTIES OF CHRL-1

Recently, Borsini and Meli (Psychopharmacology 97: 183 (1988; see also Psychopharmacology 94: 147) have reported considerable evidence of their own supported by that of a number of other investigators that the 'despair' induced by the forced swimming test originally proposed by Porsolt et al. (Eur. J. Pharmac. 47: 379 (1978) is a valid and reliable test of anti-depressant activity, provided that (1) a pretest of 15 min. duration is included and (2) the test is conducted solely in rats.

The paradigm consists of immersing rats (in the present case Sabra) in a plexiglass cylinder, 40 cm high and 18 cm in diameter, containing 15 cm of water heated to 25° C. After a 15 min. pre-test, the animals are dried for 15 min. in a heated enclosure (32° C.) and exposed again to the same conditions 24 h. later, for 5 min. Total immobility time is then recorded, where immobility is defined as the animal making only those minimal movements required to keep its head above water.

FORCED SWIMMING TEST OF PORSOLT:
Statistical Analysis

| CHRL-1 DOSE (mg · kg) | N | % DISPAIR (OVER 5 MIN) |
|---|---|---|
| 0.00 (Vehicle) | 7 | 69 ± 5 |
| 0.001 | 8 | 36 ± 9 |
| 0.05 | 9 | 32 ± 2 |
| 0.20 | 9 | 26 ± 3 |
| 0.50 | 5 | 19 ± 4 |

TABLE 6

EFFECT OF CHRL-1 ON NMDA

When N-Methyl-D-Aspartate is injected subcutaneously into mice a distinct syndrome is induced, consisting initially of sedation, followed by tremor, unilateral rotation and jumping, convulsion, and finally, death. The syndrome is highly specific to NMDA receptors and is unaffected by drugs exerting no significant inhibitory effect on these receptors. The experiments below are an extention of a pilot experiment and differ from it in using a lower dose of NMDA (115 mg/kg rather than 150 mg/kg as before), and using 9 animals per group rather than 5.

C-57/B Mice; All injections s.c.

| PARAMETER | VEHICLE (TIME FROM NMDA INJECTION) | CHRL-1 TIME FROM NMDA INJECTION | |
|---|---|---|---|
| | | 0.05 mg/kg | 0.001 mg/kg |
| Latency to Tremor | 5.7 ± 1.1 | 11.5 ± 1.2 | — |
| Latency to 1st Seizure | 12.4 ± 1.0 | — | — |
| Time from NMDA Injection to Death | 17.9 ± 1.3 | — | — |

I claim:

1. A method for providing analgesia in a mammal, comprising the step of:
    administering to said mammal a dose of between about 0.001 to about 1.0 mg/kg/day of a composition essentially of forskokin solubilized in dimethyl sulfoxide and a surface-active agent.

2. The method of claim 1, wherein said composition is administered in an amount effective to provide a dose of forskolin from about 0.001 to about 0.005 mg/kg/day.

3. The method of claim 1, wherein said composition is administered at a dose of from about 0.1 to about 1.0 mg/kg/day.

* * * * *

UNITED STATES PATENT AND TRADEMARK OFFICE
CERTIFICATE OF CORRECTION

PATENT NO. : 5,371,104

DATED : December 6, 1994

INVENTOR(S) : Jeffery J. Feigenbaum

It is certified that error appears in the above-identified patent and that said Letters Patent is hereby corrected as shown below:

Column 2, Line 7, "monoglylcerides" should be --monoglycerides--.

Column 2, Line 13, "polyoxyoxyl" should be --polyoxyl--.

Column 2, Line 29, "0.4 mn" should be --0.4 ml--.

Column 2, Line 37, "0.5 mn" should be --0.5 ml--.

"TABLE 8" should be --TABLE B--.

Column 12, Line 13, please insert --consisting-- between --composition-- and --essentially--.

Signed and Sealed this

Fourteenth Day of February, 1995

Attest:

BRUCE LEHMAN

Attesting Officer     Commissioner of Patents and Trademarks